US006451794B1

(12) United States Patent
Beswick et al.

(10) Patent No.: US 6,451,794 B1
(45) Date of Patent: Sep. 17, 2002

(54) 2,3-DIARYL-PYRAZOLO[1,5-B]PYRIDAZINES DERIVATIVES, THEIR PREPARATION AND THEIR USE AS CYCLOOXYGENASE 2(COX-2) INHIBITORS

(75) Inventors: Paul John Beswick, Hitchin; Ian Baxter Campbell, Biggleswade; Neil Mathews, Welwyn; Alan Naylor, Royston, all of (GB)

(73) Assignee: Smithkline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/508,029

(22) PCT Filed: Sep. 3, 1998

(86) PCT No.: PCT/EP98/05558

§ 371 (c)(1),
(2), (4) Date: Jun. 13, 2000

(87) PCT Pub. No.: WO99/12930

PCT Pub. Date: Mar. 18, 1999

(30) Foreign Application Priority Data

Sep. 5, 1997 (GB) ............................................... 9718792
Dec. 23, 1997 (GB) ............................................... 9727116

(51) Int. Cl.$^7$ .................. A61K 31/4985; C07D 487/04
(52) U.S. Cl. ...................................... 514/248; 544/236
(58) Field of Search .......................... 544/236; 514/248

(56) References Cited

U.S. PATENT DOCUMENTS

| | | | |
|---|---|---|---|
| 4,985,444 A | 1/1991 | Shiokawa et al. | 514/300 |
| 5,155,114 A | 10/1992 | Shiokawa et al. | 514/300 |
| 5,296,490 A | 3/1994 | Shiokawa et al. | 514/300 |
| 5,300,478 A | 4/1994 | Michaely et al. | 504/246 |
| 5,498,774 A | 3/1996 | Mistudera et al. | 504/246 |
| 5,552,422 A | 9/1996 | Gauthier et al. | 514/368 |
| 5,700,816 A | 12/1997 | Isakson et al. | 514/326 |
| 5,990,148 A | 11/1999 | Isakson et al. | 514/406 |
| 6,136,839 A | 10/2000 | Isakson et al. | 514/618 |

FOREIGN PATENT DOCUMENTS

| | | |
|---|---|---|
| EP | 364204 A1 | 4/1990 |
| EP | 0404 190 B1 | 6/1990 |
| EP | 0404 190 A1 | 6/1990 |
| EP | 467248 B1 | 1/1992 |
| WO | WO 91/00092 | 1/1991 |
| WO | WO 91/19497 | 12/1991 |
| WO | WO95 00501 A | 1/1995 |
| WO | WO96 06840 | 3/1996 |
| WO | WO96 21667 A | 7/1996 |
| WO | WO96 31509 A | 10/1996 |
| WO | WO 96/41625 | 12/1996 |
| WO | WO 96/41626 | 12/1996 |
| WO | WO96 41645 A | 12/1996 |
| WO | WO 96/41645 | 12/1996 |
| WO | WO 9912930 | 3/1999 |
| WO | WO 01/14375 A1 | 3/2001 |

OTHER PUBLICATIONS

Vane, *Pharmacology*, vol. 367, pp. 215–216, 1994.*
Talley, J.J., "Selective Inhibitors Of Cyclooxygenase–2" Expert Opinion on Therapeutic Patents, vol. 7, No. 1, Jan., 1997, pp. 55–62.
Carter, J.S., "Recently Reported Inhibitors Of Cyclooxygenase–2" Expert Opinion on Therapeutic Patents, vol. 8, No. 1, Jan. 1998, pp. 21–29.
Roy, P., "A New Series of Selective Cox–2 Inhibitors: 5,6–Diarylthiazolo[3,2–b][1,22,4] Triazoles" *Bioorganic & Med. Chem. Ltrs*, vol. 7, No. 1, 1997, pp. 57–62.
Therien, Michael, Synthesis and Biological Evaluation of 5,6–Diarylimidazo[2.1–b]Thiazole As Selective Cox–2 Inhibitors, *Bioorganic & Med. Chem. Ltrs*, vol. 7, No. 1, 1997, pp. 47–52.
Akahane, Atsushi, Discovery of 6–Oxo–3–(2–Phenylpyrazolo[1,5–a]pyridin–3–yl)–1(6H)–pyridazinebutanoic Acid (FR 838): A Novel Non–Xanthine Adenosine $A_1$ Receptor Antagonist with Potent Diuretic Activity, *Journal of Medicinal Chemistry*, vol.42, No. 5, 1999, pp. 779–783.
Talley, John J., "5 Selective Inhibitors of Cyclooxygenase–2 (COX–2)" Progress in Medicinal Chemistry, vol. 36, 1999, pp. 201–234.

* cited by examiner

Primary Examiner—Richard L. Raymond
(74) Attorney, Agent, or Firm—Lorie Ann Morgan

(57) ABSTRACT

The invention provides the compounds of formula (I) and pharmaceutically acceptable derivatives thereof in which: $R^0$ is halogen, $C_{1-6}$alkyl, $C_{1-6}$alkoxy, $C_{1-6}$alkoxy substituted by one or more fluorine atoms, or $O(CH_2)_nNR^4R^5$; $R^1$ and $R^2$ are independently selected from H, $C_{1-6}$alkyl, $C_{1-6}$alkyl, substituted by one or more fluorine atoms, $C_{1-6}$alkoxy, $C_{1-6}$hydroxyalkyl, $SC_{1-6}$alkyl, $C(O)H$, $C(O)C_{1-6}$alkyl, $C_{1-6}$alkylsulphonyl, $C_{1-6}$alkoxy substituted by one or more fluorine atoms, $O(CH_2)_nCO_2C_{1-6}$alkyl, $O(CH_2)_nSC_{1-6}$alkyl, $(CH_2)_nNR^4R^5$, $(CH_2)_nSC_{1-6}$alkyl or $C(O)NR^4R^5$; with the proviso that when $R^0$ is at the 4-position and is halogen, at least one of $R^1$ and $R^2$ is $C_{1-6}$alkylsulphonyl, $C_{1-6}$alkoxy substituted by one or more fluorine atoms, $O(CH_2)_nCO_2C_{1-6}$alkyl, $O(CH_2)_nSC_{1-6}$alkyl, $(CH_2)_nNR^4R^5$ or $(CH_2)_nSC_{1-6}$alkyl, $C(O)NR^4R^5$; $R^3$ is $C_{1-6}$alkyl or $NH^2$; $R^4$ and $R^5$ are independently selected from H, or $C_{1-6}$alkyl or, together with the nitrogen atom to which they are attached, form a 4–8 membered saturated ring; and n is 1–4. Compounds of formula (I) are potent and selective inhibitors of COX-2 and are of use in the treatment of the pain, fever, inflammation of a variety of conditions and diseases.

(I)

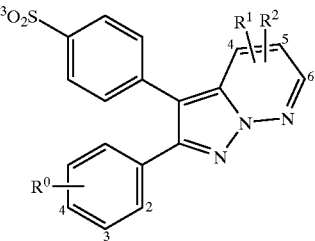

34 Claims, No Drawings

2,3-DIARYL-PYRAZOLO[1,5-B]PYRIDAZINES DERIVATIVES, THEIR PREPARATION AND THEIR USE AS CYCLOOXYGENASE 2(COX-2) INHIBITORS

This application is a 371 application of PTC/EP98/05558, filed Sep. 3, 1998.

This invention relates to pyrazolo[1,5-b]pyridazine derivatives, to processes for their preparation, to pharmaceutical compositions containing them and to their use in medicine.

The enzyme cyclooxygenase (COX) has recently been discovered to exist in two isoforms, COX-1 and COX-2. COX-1 corresponds to the originally identified constitutive enzyme while COX-2 is rapidly and readily inducible by a number of agents including mitogens, endotoxin, hormones, cytokines and growth factors. Prostaglandins generated by the action of COX have both physiological and pathological roles. It is generally believed that COX-1 is responsible for the important physiological functions such as maintenance of gastrointestinal integrity and renal blood flow. In contrast the inducible form, COX-2, is believed to be responsible for the pathological effects of prostaglandins where rapid induction of the enzyme occurs in response to such agents as inflammatory agents, hormones, growth factors and cytokines. A selective inhibitor of COX-2 would therefore have anti-inflammatory, anti-pyretic and analgesic properties, without the potential side effects associated with inhibition of COX-1. We have now found a novel group of compounds which are both potent and selective inhibitors of COX-2.

The invention thus provides the compounds of formula (I)

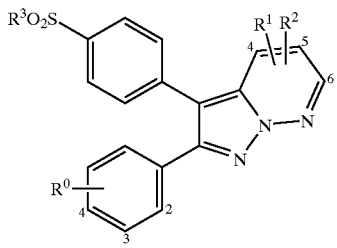

and pharmaceutically acceptable derivatives thereof in which:

$R^0$ is halogen, $C_{1-6}$alkyl, $C_{1-6}$alkoxy, $C_{1-6}$alkoxy substituted by one or more fluorine atoms, or $O(CH_2)_nNR^4R^5$;

$R^1$ and $R^2$ are independently selected from H, $C_{1-6}$alkyl, $C_{1-6}$alkyl substituted by one or more fluorine atoms, $C_{1-6}$alkoxy, $C_{1-6}$hydroxyalkyl, $SC_{1-6}$alkyl, $C(O)H$, $C(O)C_{1-6}$alkyl, $C_{1-6}$alkylsulphonyl, $C_{1-6}$alkoxy substituted by one or more fluorine atoms, $O(CH_2)_nCO_2C_{1-6}$alkyl, $O(CH_2)_nSC_{1-6}$alkyl, $(CH_2)_nNR^4R^5$, $(CH_2)_nSC_{1-6}$alkyl or $C(O)NR^4R^5$; with the proviso that when $R^0$ is at the 4-position and is halogen, at least one of $R^1$ and $R^2$ is $C_{1-6}$alkylsulphonyl, $C_{1-6}$alkoxy substituted by one or more fluorine atoms, $O(CH_2)_nCO_2C_{1-6}$alkyl, $O(CH_2)_nSC_{1-6}$alkyl, $(CH_2)_nNR^4R^5$ or $(CH_2)_nSC_{1-6}$alkyl, $C(O)NR^4R^5$;

$R^3$ is $C_{1-6}$alkyl or $NH_2$;

$R^4$ and $R^5$ are independently selected from H, or $C_{1-6}$alkyl or, together with the nitrogen atom to which they are attached, form a 4–8 membered saturated ring; and n is 1–4.

By pharmaceutically acceptable derivative is meant any pharmaceutically acceptable salt, solvate or ester, or salt or solvate of such ester, of the compounds of formula (I), or any other compound which upon administration to the recipient is capable of providing (directly or indirectly) a compound of formula (I) or an active metabolite or residue thereof.

It will be appreciated that, for pharmaceutical use, the salts referred to above will be the physiologically acceptable salts, but other salts may find use, for example in the preparation of compounds of formula (I) and the physiologically acceptable salts thereof.

Suitable pharmaceutically acceptable salts of the compounds of formula (I) include acid addition salts formed with inorganic or organic acids, preferably inorganic acids, e.g. hydrochlorides, hydrobromides and sulphates.

The term halogen is used to represent fluorine, chlorine, bromine or iodine. The term 'alkyl' as a group or part of a group means a straight or branched chain alkyl group, for example a methyl, ethyl, n-propyl, i-propyl, n-butyl, s-butyl or t-butyl group.

Preferably, $R^0$ is at the 3- or 4-position of the phenyl ring, as defined in formula (I).

Preferably, $R^1$ is at the 6-position of the pyridazine ring, as defined in formula (I).

Preferably, $R^0$ is F, $C_{1-3}$alkyl, $C_{1-3}$alkoxy, $C_{1-3}$alkoxy substituted by one or more fluorine atoms, or $O(CH_2)_{1-3}NR^4R^5$. More preferably $R^0$ is F, $C_{1-3}$alkoxy or $C_{1-3}$alkoxy substituted by one or more fluorine atoms.

Preferably, $R^1$ is $C_{1-4}$alkylsulphonyl, $C_{1-4}$alkoxy substituted by one or more fluorine atoms, $O(CH_2)_{1-3}CO_2C_{1-4}$alkyl, $O(CH_2)_{1-3}SC_{1-4}$alkyl, $(CH_2)_{1-3}NR^4R^5$, $(CH_2)_{1-3}SC_{1-4}$alkyl or $C(O)NR^4R^5$ or, when $R^0$ is $C_{1-6}$alkyl, $C_{1-6}$alkoxy, $O(CH_2)_nNR^4R^5$, may also be H. More preferably $R^1$ is $C_{1-4}$alkylsulphonyl, $C_{1-4}$alkoxy substituted by one or more fluorine atoms or, when $R^0$ is $C_{1-6}$alkyl, $C_{1-6}$alkoxy, $C_{1-6}$alkoxy substituted by one or more fluorine atoms, or $O(CH_2)_nNR^4R^5$, may also be H.

Preferably, $R^2$ is H.

Preferably, $R^3$ is methyl or $NH_2$.

Preferably, $R^4$ and $R^5$ are independently $C_{1-3}$alkyl or, together with the nitrogen atom to which they are attached, form a 5–6 membered saturated ring.

Preferably, n is 1–3, more preferably 1 or 2.

Within the invention there is provided one group of compounds of formula (I) (group A) wherein: $R^0$ is F, $C_{1-3}$alkyl, $C_{1-3}$alkoxy, $C_{1-3}$alkoxy substituted by one or more fluorine atoms, or $O(CH_2)_nNR^4R^5$; $R^1$ is $C_{1-6}$alkylsulphonyl, $C_{1-4}$alkoxy substituted by one or more fluorine atoms, $O(CH_2)_nCO_2C_{1-4}$alkyl, $O(CH_2)_nSC_{1-4}$alkyl, $(CH_2)_nNR^4R^5$, $(CH_2)_nSC_{1-4}$alkyl or $C(O)NR^4R^5$ or, when $R^0$ is $C_{1-3}$alkyl, $C_{1-3}$alkoxy, $C_{1-3}$alkoxy substituted by one or more fluorine atoms, or $O(CH_2)_nNR^4R^5$, may also be H; $R^2$ is H; $R^3$ is methyl or $NH_2$; $R^4$ and $R^5$ are independently $C_{1-3}$alkyl or, together with the nitrogen atom to which they are attached, form a 5–6 membered saturated ring; and n is 1–3.

Within group A, there is provided another group of compounds (group A1) wherein $R^0$ is F, methyl, $C_{1-2}$alkoxy, $OCHF_2$; or $O(CH_2)_nNR^4R^5$; $R^1$ is methylsulphonyl, $OCHF_2$, $O(CH_2)_nCO_2C_{1-4}$alkyl, $O(CH_2)_nSCH_3$, $(CH_2)_nNR^4R^5$, $(CH_2)_nSCH_3$ or $C(O)NR^4R^5$ or, when $R^0$ is methyl, $C_{1-2}$alkoxy, $OCHF_2$, or $O(CH_2)_nN(CH_3)_2$, may also be H; $R^2$ is H; $R^3$ is methyl or $NH_2$; $R^4$ and $R^5$ are both methyl or, together with the nitrogen atom to which they are attached, form a 5–6 membered saturated ring; and n is 1–2.

Within group A, there is provided a further group of compounds (group A2) wherein $R^0$ is F, $C_{1-3}$alkoxy or $C_{1-3}$alkoxy substituted by one or more fluorine atoms; $R^1$ is $C_{1-4}$alkylsulphonyl, $C_{1-4}$alkoxy substituted by one or more fluorine atoms or, when $R^0$ $C_{1-3}$alkoxy or $C_{1-3}$alkoxy substituted by one or more fluorine atoms, may also be H; $R^2$ is H; and $R^3$ is methyl or $NH_2$.

Within groups A, A1 and A2, $R^0$ is preferably at the 3- or 4-position of the phenyl ring and $R^2$ is preferably at the 6-position of the pyridazine ring.

It is to be understood that the present invention encompasses all isomers of the compounds of formula (I) and their pharmaceutically acceptable derivatives, including all geometric, tautomeric and optical forms, and mixtures thereof (e.g. racemic mixtures).

Particularly preferred compounds of the invention are:
- 3-(4-methanesulfonyl-phenyl)-2-(4-methoxy-phenyl)-pyrazolo[1,5-b]pyridazine;
- 6-difluoromethoxy-2-(4-fluoro-phenyl)-3-(4-methanesulfonyl-phenyl)-pyrazolo[1,5-b]pyridazine;
- 2-(4-ethoxy-phenyl)-3-(4-methanesulfonyl-phenyl)-pyrazolo[1,5-b]pyridazine;
- 2-(4-fluoro-phenyl)-6-methanesulfonyl-3-(4-methanesulfonyl-phenyl)-pyrazolo[1,5-b]pyridazine;
- 2-(4-difluoromethoxy-phenyl)-3-(4-methanesulfonyl-phenyl)-pyrazolo[1,5-b]pyridazine;
- 4-[2-(4-ethoxy-phenyl)-pyrazolo[1,5-b]pyridazin-3-yl]-benzenesulfonamide;
- 6-difluoromethoxy-2-(3-fluoro-phenyl)-3-(4-methanesulfonyl-phenyl)-pyrazolo[1,5-b]pyridazine;

and pharmaceutically acceptable derivatives thereof.

Compounds of the invention are potent and selective inhibitors of COX-2. This activity is illustrated by their ability to selectively inhibit COX-2 over COX-1.

In view of their selective COX-2 inhibitory activity, the compounds of the present invention are of interest for use in human and veterinary medicine, particularly in the treatment of the pain (both chronic and acute), fever and inflammation of a variety of conditions and diseases. Such conditions and diseases are well known in the art and include rheumatic fever; symptoms associated with influenza or other viral infections, such as the common cold; lower back and neck pain; headache; toothache; sprains and strains; myositis; neuralgia; synovitis; arthritis, including rheumatoid arthritis; degenerative joint diseases, including osteoarthritis; gout and ankylosing spondylitis; tendinitis; bursitis; skin related conditions, such as psoriasis, eczema, burns and dermatitis; injuries, such as sports injuries and those arising from surgical and dental procedures.

The compounds of the invention may also be useful for the treatment of other conditions mediated by selective inhibition of COX-2.

For example, the compounds of the invention may inhibit cellular and neoplastic transformation and metastatic tumour growth and hence be useful in the treatment of certain cancerous diseases, such as colonic cancer.

Compounds of the invention may also prevent neuronal injury by inhibiting the generation of neuronal free radicals (and hence oxidative stress) and therefore may be of use in the treatment of stroke; epilepsy; and epileptic seizures (including grand mal, petit mal, myoclonic epilepsy and partial seizures).

Compounds of the invention also inhibit prostanoid-induced smooth muscle contraction and hence may be of use in the treatment of dysmenorrhoea and premature labour.

Compounds of the invention inhibit inflammatory processes and therefore may be of use in the treatment of asthma, allergic rhinitis and respiratory distress syndrome; gastrointestinal conditions such as inflammatory bowel disease, Chron's disease, gastritis, irritable bowel syndrome and ulcerative colitis; and the inflammation in such diseases as vascular disease, migraine, periarteritis nodosa, thyroiditis, aplastic anemia, Hodgkin's disease, sclerodoma, type I diabetes, myasthenia gravis, multiple sclerosis, sorcoidosis, nephrotic syndrome, Bechet's syndrome, polymyositis, gingivitis, conjunctivitis and myocardial ischemia.

Compounds of the invention may also be useful in the treatment of ophthalmic diseases such as retinitis, retinopathies, uveitis and of acute injury to the eye tissue.

Compounds of the invention may also be useful for the treatment of cognitive disorders such as dementia, particularly degenerative dementia (including senile dementia, Atzheimer's disease, Pick's disease, Huntington's chorea, Parkinson's disease and Creutzfeldt-Jakob disease), and vascular dementia (including multi-infarct dementia), as well as dementia associated with intracranial space occupying lesions, trauma, infections and related conditions (including HIV infection), metabolism, toxins, anoxia and vitamin deficiency; and mild cognitive impairment associated with ageing, particularly Age Associated Memory Impairment.

According to a further aspect of the invention, we provide a compound of formula (I) or a pharmaceutically acceptable derivative thereof for use in human or veterinary medicine.

According to another aspect of the invention, we provide a compound of formula (I) or a pharmaceutically acceptable derivative thereof for use in the treatment of a condition which is mediated by selective inhibition of COX-2.

According to a further aspect of the invention, we provide a method of treating a human or animal subject suffering from a condition which is mediated by selective inhibition of COX-2 which comprises administering to said subject an effective amount of a compound of formula (I) or a pharmaceutically acceptable derivative.

According to another aspect of the invention, we provide the use of a compound of formula (I) or a pharmaceutically acceptable derivative thereof for the manufacture of a therapeutic agent for the treatment of a condition which is mediated by selective inhibition of COX-2, such as an inflammatory disorder.

According to a further aspect of the invention, we provide a method of treating a human or animal subject suffering from an inflammatory disorder, which method comprises administering to said subject an effective amount of a compound of formula (I) or a pharmaceutically acceptable derivative thereof.

It is to be understood that reference to treatment includes both treatment of established symptoms and prophylactic treatment, unless explicitly stated otherwise.

It will be appreciated that the compounds of the invention may advantageously be used in conjunction with one or more other therapeutic agents. Examples of suitable agents for adjunctive therapy include pain relievers such as a glycine antagonist, a sodium channel inhibitor (e.g. lamotrigine), a substance P antagonist (e.g. an $NK_1$ antagonist), acetaminophen or phenacetin; a matrix metalloproteinase inhibitor; a nitric oxide synthase (NOS) inhibitor (e.g. an iNOS or an nNOS inhibitor); an inhibitor of the release, or action, of tumour necrosis factor α; an antibody therapy (e.g. a monoclonal antibody therapy); a stimulant, including caffeine; an $H_2$-antagonist, such as ranitidine; a proton pump inhibitor, such as omeprazole; an antacid, such as aluminium or magnesium hydroxide; an anfiflatulent, such as simethicone; a decongestant, such as phenylephrine, phenylpropanolamine, pseudoephedrine, oxymetazoline, epinephrine, naphazoline, xylometazoline, propylhexedrine, or levo-desoxyephedrine; an antitussive, such as codeine, hydrocodone, carmiphen, carbetapentane, or dextramethorphan; a diuretic; or a sedating or non-sedating antihistamine. It is to be understood that the present invention covers the use of a compound of formula (I) or a pharmaceutically acceptable derivative thereof in combination with one or more other therapeutic agents.

The compounds of formula (I) and their pharmaceutically acceptable derivatives are conveniently administered in the form of pharmaceutical compositions. Thus, in another aspect of the invention, we provide a pharmaceutical composition comprising a compound of formula (I) or a pharmaceutically acceptable derivative thereof adapted for use in human or veterinary medicine. Such compositions may conveniently be presented for use in conventional manner in admixture with one or more physiologically acceptable carriers or excipients.

The compounds of formula (I) and their pharmaceutically acceptable derivatives may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable derivatives.

For oral administration, the pharmaceutical composition may take the form of, for example, tablets (including sublingual tablets), capsules, powders, solutions, syrups or suspensions prepared by conventional means with acceptable excipients.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilising and/or dispersing agents. For administration by injection these may take the form of a unit dose presentation or as a multidose presentation preferably with an added preservative.

Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

As stated above, the compounds of the invention may also be used in combination with other therapeutic agents. The invention thus provides, in a further aspect, a combination comprising a compound of formula (I) or a pharmaceutically acceptable derivative thereof together with a further therapeutic agent.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A proposed daily dosage of a compound of formula (I) for the treatment of man is 0.01 mg/kg to 500 mg/kg, such as 0.05 mg/kg to 100 mg/kg, e.g. 0.1 mg/kg to 50 mg/kg, which may be conveniently administered in 1 to 4 doses. The precise dose employed will depend on the age and condition of the patient and on the route of administration. Thus, for example, a daily dose of 0.25 mg/kg to 10 mg/kg may be suitable for systemic administration.

Compounds of formula (I) and pharmaceutically acceptable derivatives thereof may be prepared by any method known in the art for the preparation of compounds of analogous structure.

Suitable methods for the preparation of compounds of formula (I) and pharmaceutically acceptable derivatives thereof are described below. In the formulae that follow $R^0$ to $R^5$ and n are as defined in formula (I) above unless otherwise stated; Hal is a halogen, such as Br or I; $X^-$ is a counterion, such as $I^-$; and alkyl is as previously defined.

Thus according to a first process (A), compounds of formula (I) may be prepared by reacting a compound of formula (II)

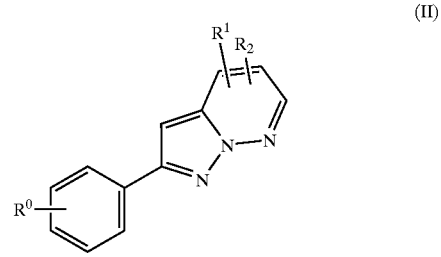

or a protected derivative thereof with a boronic acid of formula (III)

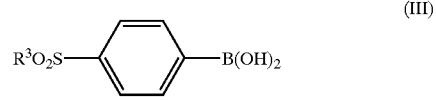

or a suitable derivative thereof in the presence of a suitable transition metal catalyst. Suitable derivatives of formula (III) include boronic acid esters, such as those described in R. Miyaura et al, J. Org. Chem., 1995, 60, 7508–7510. Conveniently, the reaction is carried out in a solvent, such as an ether (e.g. 1,2 dimethoxyethane); in the presence of a base, such as an inorganic base (e.g. sodium carbonate); and employing a palladium catalyst, such as tetrakis (triphenylphosphine)palladium(0).

According to a another process (B), compounds of formula (I) wherein $R^3$ is $C_{1-6}$alkyl may be prepared by oxidising a compound of formula (IV)

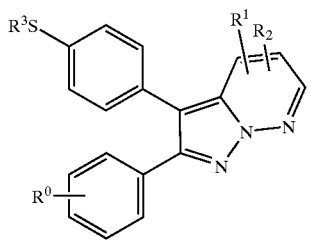

(IV)

or a protected derivative thereof under conventional conditions. Conveniently the oxidation is effected using a monopersulfate compound, such as potassium peroxymonosulfate (known as Oxone™) and the reaction is carried out in a solvent, such as an aqueous alcohol, (e.g. aqueous methanol), and at between −78° C. and ambient temperature.

According to a another process (C), compounds of formula (I) wherein $R^1$ is $C_{1-6}$alkylsulphonyl may be prepared by oxidising a compound of formula (V)

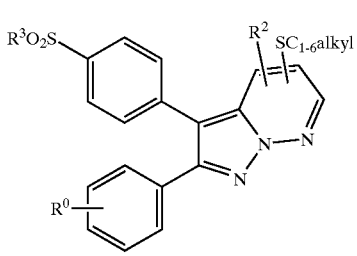

(V)

or a protected derivative thereof under conventional conditions. Conveniently the oxidation is effected in the manner described just above for process (B).

According to a another process (D), compounds of formula (I) wherein $R^1$ is $C_{1-6}$alkoxy substituted by one or more fluorine atoms may be prepared by reacting an alcohol of formula (VI)

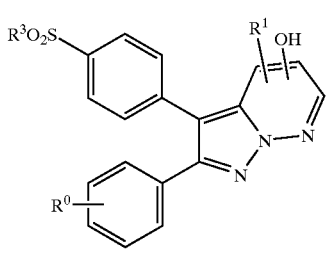

(VI)

or a protected derivative thereof with a halofluoroalkane under conventional conditions. Conveniently the reaction is effected in a solvent, such as a polar solvent (e.g. N,N-dimethylformamide), in the presence of a strong base, such as an inorganic hydride (e.g. sodium hydride), at about ambient temperature and using the appropriate bromofluoroalkane to give the desired compound of formula (I).

According to another process (E) compounds of formula (I) may be prepared by interconversion, utilising other compounds of formula (I) as precursors. The following procedures are illustrative of suitable interconversions.

Compounds of formula (I) wherein $R^1$ or $R^2$ represent $C_{1-6}$alkyl substituted by one or more fluorine atoms may be prepared from the appropriate compound of formula (I) wherein $R^1$ or $R^2$ is $C_{1-6}$hydroxyalkyl, C(O)H or C(O)$C_{1-6}$alkyl, by treatment with a suitable source of fluorine. Suitable sources of fluorine include, for example, diethylaminosulphur trifluoride. Conveniently the reaction is effected in the presence of a solvent, such as a halogenated hydrocarbon (e.g. dichloromethane), and at reduced temperature, such as −78° C.

Compounds of formula (I) wherein $R^1$ or $R^2$ represent C(O)H may be prepared from the corresponding compound of formula (I) wherein $R^1$ or $R^2$ represent $CH_2OH$ by oxidation. Suitable oxidising agents include, for example, manganese (IV) oxide. Conveniently the oxidation is effected in the presence of a solvent, such as a halogenated hydrocarbon (e.g. chloroform), and at elevated temperature (e.g. reflux).

Compounds of formula (I) wherein $R^1$ or $R^2$ represent $C_{1-6}$hydroxyalkyl, and wherein the hydroxy group is attached to the carbon linked to the pyridazine ring, may be prepared by reduction of the compound of formula (I) wherein $R^1$ or $R^2$ represent the corresponding aldehyde or ketone. Suitable reducing agents include hydride reducing agents, such as diisobutylaluminium hydride.

Conveniently the reduction is effected in the presence of a solvent, such as a halogenated hydrocarbon (e.g. dichloromethane), and at reduced temperature, such as −78° C.

As will be appreciated by those skilled in the art it may be necessary or desirable at any stage in the synthesis of compounds of formula (I) to protect one or more sensitive groups in the molecule so as to prevent undesirable side reactions.

Another process (F) for preparing compounds of formula (I) thus comprises deprotecting protected derivatives of compounds of formula (I).

The protecting groups used in the preparation of compounds of formula (I) may be used in conventional manner. See, for example, those described in 'Protective Groups in Organic Synthesis' by Theodora W. Greene and Peter G. M. Wuts, second edition, (John Wiley and Sons, 1991), which also describes methods for the removal of such groups.

Compounds of formula (II) may be prepared by halogenating compounds of formula (VII)

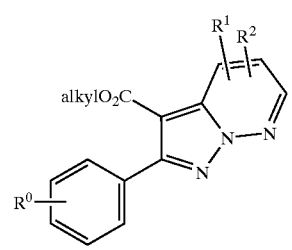

(VII)

by conventional means.

Thus esters of formula (VI) are first hydrolysed to their corresponding acids, for example by treatment with a strong base (e.g. sodium hydroxide), in the present of a solvent (e.g. ethanol) and at elevated temperature. The corresponding acid is then treated with a halogenating agent, conveniently at ambient temperature and in a solvent (e.g. chlorinated hydrocarbon), under which conditions the acid undergoes both halogenation and decarboxylation. Conveniently, the halogenating agent is a brominating agent, such as bromine in the presence of a strong acid (e.g. hydrobromic acid in acetic acid) or N-bromosuccinimide, to yield the corresponding compound of formula (II) wherein Hal is bromine.

Esters of formula (VII) may be prepared by reacting a compound of formula (VIII)

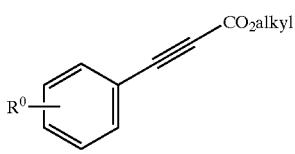

with an aminopyridazinium complex of formula (IX)

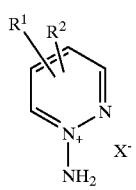

under conventional conditions. Conveniently the reaction is effected in the presence of a base, such as potassium carbonate, a solvent, such as N,N-dimethylformamide and at ambient temperature.

Boronic acids of formula (III) are either known compounds or may be prepared by literature methods such as those described in, for example, EPA publication No.533268.

Compounds of formulae (IV), (V) and (VI) may be prepared by methods analogous to those described for the preparation of the compound of formula (I) from compounds of formula (II).

Compounds of formula (VIII) are either known compounds or may be prepared by literature methods such as those described in, for example, D H Wadsworth et al, J Org Chem, (1987), 52(16), 3662–8 and J. Morris and D. G. Wishka, Synthesis (1994), (1), 43–6.

Compounds of formula (IX) are either known compounds or may be prepared by literature methods such as those described in, for example, Y Kobayashi et al, Chem Pharm Bull, (1971), 19(10), 2106–15; T. Tsuchiya, J. Kurita and K. Takayama, Chem. Pharm. Bull. 28(9) 2676–2681 (1980) and K Novitskii et al, Khim Geterotskil Soedin, 1970 2, 57–62.

Certain intermediates described above are novel compounds, and it is to be understood that all novel intermediates herein form further aspects of the present invention. Compounds of formula (II) are key intermediates and represent a particular aspect of the present invention.

Conveniently, compounds of the invention are isolated following work-up in the form of the free base. Pharmaceutically acceptable acid addition salts of the compounds of the invention may be prepared using conventional means.

Solvates (e.g. hydrates) of a compound of the invention may be formed during the work-up procedure of one of the aforementioned process steps.

The following Examples illustrate the invention but do not limit the invention in any way. All temperatures are in °C. Flash column chromatography was carried out using Merck 9385 silica. Thin layer chromatography (Tlc) was carried out on silica plates. NMR was carried out on a Brucker 250 MHz spectrometer. Chemical shifts are given, with respect to tetramethylsilane as internal chemical shift reference, in δ ppm. The following abbreviations are used: Me=methyl, s=singlet, d=doublet, t=triplet and m=multiplet.

EXAMPLE 1

6-Difluoromethoxy-2-(4-fluoro-phenyl)-3-(4-methanesulfonyl-phenyl)-pyrazolo[1,5-b]pyridazine (i) 6-Methoxy-2-(4-fluoro-phenyl-pyrazolo[1,5-b]pyridazine-3-carboxylic Acid Methyl Ester.

1,8-Diazabicyclo[5.4.0]undec-7-ene (3.39 ml) was added to a mixture of 3-(4-fluorophenyl)-prop-2-ynoic acid methyl ester (3.36 g) and 1-amino-3-methoxy-pyridazin-1-ium mesitylene sulphonate[1] (6.1419 g) in acetonitrile (125 ml) and the mixture was stirred at ambient temperature for 48 hours. During the first 2 hours a stream of air was passed through the reaction. The mixture was concentrated in vacuo, dissolved in ethyl acetate (150 ml), washed with water (3×25 ml), dried (MgSO$_4$), filtered and evaporated in vacuo to give the title compound as a brown solid (4.77 g).

$^1$H NMR (CDCl$_3$): 8.4 (d, 1H, J=10 Hz) 7.85–7.90 (m, 2H) 7.1–7.2 (m, 2H) 6.9–7.0 (d, 1H, J=10 Hz) 4.1 (s, 3H) 3.9 (s, 3H); MH$^+$ 302; Ref:[1] T. Tsuchiya, J. Kurita and K. Takayama, Chem. Pharm. Bull. 28(9) 2676–2681 (1980).

(ii) 6-Methoxy-2-(4-fluoro-phenyl-pyrazolo[1,5-b]pyridazine-3-carboxylic Acid

A mixture of 6-methoxy-2-(4-fluoro-phenyl-pyrazolo[1,5-b]pyridazine-3-carboxylic acid methyl ester (4.469 g), 2N sodium hydroxide (50 ml) and methanol (90 ml) was heated at reflux for 2 hours. The cooled solution was added to 2N hydrochloric acid (200 ml) and the title compound was isolated by filtration as a beige solid (3.639 g).

$^1$H NMR (DMSO-d$_6$): 12.8 (br. s, 1H) 8.4 (d, 1H, J=10 Hz) 7.8–7.9 (m, 2H) 7.21–7.32 (m, 2H) 7.15–7.2 (d, 1H, J=10 Hz) 4.0 (s, 3H); MH$^+$ 288.

(iii) 2-(4-Fluoro-phenyl)-3-(4-methanesulfonyl-phenyl)-6-methoxy-pyrazolo[1,5-b]pyridazine A mixture of 6-methoxy-2-(4-fluoro-phenyl-pyrazolo[1,5-b]pyridazine-3-carboxylic acid (869 mg) and sodium bicarbonate (756 mg) in dimethylformamide (10 ml) was treated with N-bromosuccinimide (587 mg) and stirred at ambient temperature for 1 hour, then added to water (50 ml) and extracted with ethyl acetate (3×50 ml), dried (MgSO$_4$), and evaporated in vacuo. The resulting brown solid (1.612 g) was dissolved in 1,2 dimethoxyethane (20 ml). 2N Aqueous sodium carbonate solution (10 ml) was added together with 4-(methanesulphonyl)phenyl boronic acid (660 mg) and tetrakis(triphenylphosphine)palladium(0) (100 mg) and the mixture was heated at reflux for 20 hours. The reaction was poured into water (50 ml), extracted with dichloromethane (3×100 ml). The combined organic extracts were dried (MgSO$_4$) and evaporated in vacuo to give a brown solid (1.116 g) which was purified by flash column chromatography on silica, eluting with cyclohexane/ethyl acetate (4:1 then 2:1), to give the title compound as a yellow solid (390 mg).

Tlc, SiO$_2$, R$_f$ 0.3 (1:1 cyclohexane/ethyl acetate), detection UV; MH$^+$ 398.

(iv) 2-(4-Fluoro-phenyl)-3-(4-methanesulfonyl-phenyl)-pyrazolo[1,5-b]pyridazin-6-ol A mixture of 2-(4-fluoro-phenyl)-3-(4-methanesulfonyl-phenyl)-6-methoxy-pyrazolo[1,5-b]pyridazine (321 mg) and pyridine hydrochloride (1.4 g) was heated to and at 200° C. in a sealed vessel (Reactivial™) for 3 hours. The cooled reaction was poured into water (20 ml), and extracted with ethyl acetate (3×30 ml). The combined organic extracts dried (MgSO$_4$), filtered and evaporated in vacuo to give a solid which was triturated with diethyl ether to give the title compound as a beige solid (119 mg). Tlc, SiO$_2$, Rf 0.07 (1:2 cyclohexane/ethyl acetate), detection UV. MH$^+$ 384.

(v) 6-Difluoromethoxy-2-(4-fluoro-phenyl)-3-(4-methanesulfonyl-phenyl)-pyrazolo[1,5-b]pyridazine A solution of 2-(4-fluoro-phenyl)-3-(4-methanesulfonyl-phenyl)-pyrazolo[1,5-b]pyridazin-6-ol (0.2 9) in anhydrous dimethyl formamide (5 ml) was treated with sodium hydride (0.046 g, 60% dispersion in mineral oil), after effervescence ceased a stream of bromodifluoromethane gas was passed through the mixture at ambient temperature for 30 minutes. The reaction mixture was then poured into water (50 ml) and extracted with ethyl acetate (50 ml), the organic extract was washed with water (3×50 ml), dried and concentrated in vacuo. The residue was purified by chromatography to give the title compound as a white solid (0.17 g).

$MH^+$=434; 1H NMR ($CDCl_3$): δ 8.05–8.0 (d, J=10 HZ, 2H) 8.0–7.95 (d, J=10 HZ, 1H) 7.6–7.5 (m, 4H) 7.8–7.2 (t, J=70 HZ, 1H) 7.1–7.05 (t, J=11 HZ, 2H) 6.9–6.85 (d, J=10 HZ, 1H) 3.15(s,3H);

Tlc, $SiO_2$, Rf 0.35(ethyl acetate/cyclohexane(1/1)).

EXAMPLE 2

3-(4-Methanesulfonyl-phenyl)-2-(4-methoxy-phenyl)-pyrazolo[1,5-b]pyridazine (i) 2-(4-Methoxy-phenyl)-pyrazolo[1,5-b]pyridazine-3-carboxylic Acid Methyl Ester Diazabicyclo[5.4.0]undec-7-ene (22.76 ml, 2 eq) was added dropwise to a solution of methyl 3-(4-methoxy-phenyl)-prop-2-ynoic acid[1] (14.46 g, 76 mM) and 1-amino pyridazinium iodide[2] (2 eq) in acetonitrile under nitrogen and stirred for 6 h. Purification by chromatography on silica gel eluting with toluene, then toluene:ethyl acetate (9:1) gave the title compound (2.76 g) as a brown solid.

$MH^+$ 284; 1H NMR ($CDCl_3$) δ 3.87 (3H, s) 3.9 (3H, s) 7.0 (2H, d, J=9 Hz) 7.25 (1H, dd, J=9 & 4 Hz) 7.90 (2H, d, J=9 Hz) 8.45 (1H, dd, J=4 & 2 Hz) 8.55 (1H, dd, J=9 & 2 Hz); Ref:[1] J. Morris and D. G. Wishka, Synthesis (1994), (1), 43–6; Ref:[2] Kobayashi et al Chem. Pharm. Bull. (1971), 19(10), 2106–15.

(ii) 3-(4-Methanesulfonyl-phenyl)-2-(4-methoxy-phenyl)-pyrazolo[1,5-b]pyridazine A mixture of 2-(4-methoxy-phenyl)-pyrazolo[1,5-b] pyridazine-3-carboxylic acid methyl ester (2.76 g) and aq. sodium hydroxide (2N, 30 ml) in ethanol (30 ml) was refluxed under nitrogen for 2 h. The cooled mixture was acidified with hydrochloric acid (2N) and the resulting white solid (2.53 g) isolated by filtration. This solid was dissolved in DMF and sodium bicarbonate (2.67 g, 3.3 eq) added, followed by N-bromosuccinimide (1.88 g, 1.1 eq) portionwise. After stirring for 1 h under nitrogen, water was added and extracted into ethyl acetate (2×25 ml). The dried organic phase was concentrated and the residue taken up in DME (60 ml). Aqueous sodium carbonate (2N, 15 ml) was added, followed by 4-methanesulfonyl-phenylboronic acid (3.1 2 g) and tetrakis(triphenylphosphine)palladium(0) (250 mg). The mixture was heated at reflux under nitrogen for 18 h, cooled, poured into water and extracted into ethyl acetate (2×25 ml). The combined organic phases were dried and concentrated onto silica gel. Chromatography on silica gel eluting with toluene:ethyl acetate (8:1) gave, on concentration, the title compound (3.58 g) as a cream solid.

$MH^+$ 380; 1H NMR (DMSO) δ 3.25 (3H, s) 3.75 (3H, s) 6.95 (2H, d, J=8.5 Hz) 7.25 (1H, dd, J=9 & 5 Hz) 7.45 (2H, d, J=8.5 Hz) 7.60 (2H, d, J=8 Hz) 7.9 (2H, d, J=8.5 Hz) 8.15 (1H, dd, J=9 & 2 Hz) 8.49 (1H, dd, J=5 & 2 Hz).

EXAMPLE 3

2-(4-Ethoxy-phenyl)-3-(4-methanesulfonyl-phenyl)-pyrazolo[1,5-b]pyridazine (i) 4-[3-(4-Methanesulfonyl-phenyl)-pyrazolo[1,5-b]pyridazin-2-yl]-phenol Boron tribromide (1M solution in $CH_2Cl_2$, 2.1 eq) was added to 3-(4-methanesulfonyl-phenyl)-2-(4-methoxy-phenyl)-pyrazolo[1,5-b]pyridazine (3.58 g) in $CH_2Cl_2$ at −70°. The mixture was stirred for 10 min then warmed to 0° and stirred at 0° overnight. The reaction mixture was made alkaline with potassium carbonate then acidified with hydrochloric acid (2M), poured into water and extracted into $CH_2Cl_2$. The organic phase was dried, filtered and concentrated to give the title compound (1.87 g) as a yellow solid.

$MH^+$ 366; 1H NMR (DMSO) δ 3.30 (3H, s) 6.80 (2H, d, J=8.5 Hz) 7.30 (1H, dd, J=9 & 5 Hz) 7.35 (2H, d, J=8.5 Hz) 7.60 (2H, d, J=8 Hz) 8.0 (2H, d, J=8.5 Hz) 8.20 (1H, dd, J=9 & 2 Hz) 8.55 (1H, dd, J=5 & 2 Hz) 9.75 (1H, s).

(ii) 2-(4-Ethoxy-phenyl)-3-(4-methanesulfonyl-phenyl)-pyrazolo[1,5-b]pyridazine

4-[3-(4-Methanesulfonyl-phenyl)-pyrazolo[1,5-b] pyridazin-2-yl]-phenol (663 mg, 1.82), iodoethane (1 eq) and potassium carbonate (2 eq) in acetonitrile (30 ml) were heated at reflux under nitrogen for 18 h. The cooled reaction mixture was partitioned between water (30 ml) and ethyl acetate (30 ml). The organic phase was collected, dried and purified by chromatography to give the title compound (547 mg) as a cream foam.

$MH^+$ 394; 1H NMR (DMSO) δ 1.45 (3H, t, J=7 Hz) 3.10 (3H, s) 4.1 (2H, q, J=7 Hz) 6.87 (2H, d, J=9 Hz) 7.08 (1H, dd, J=9 & 5 Hz) 7.55 (4H, t, J=9 Hz) 7.92.(1H, dd, J=9 & 2 Hz) 7.95 (2H, d, J=9 Hz) 8.20 (1H, dd, J=9 & 2 Hz) 8.32 (1H, dd, J=5 & 2 Hz).

EXAMPLE 4

2-(4-Fluoro-phenyl)-6-methanesulfonyl-3-(4-methanesulfonyl-phenyl)-pyrazolo[1,5-b]pyridazine (i) 2-(4-Fluoro-phenyl)-6-methylsulfanyl-pyrazolo[1,5-b]pyridazine-3-carboxylic Acid Methyl Ester Solid t-butoxycarbonyl-O-mesitylenesufonylhydroxylamine[1] (7.8 g) was added portionwise with stirring to TFA (25 ml) over 10 min then stirred for a further 20 minutes. The solution was poured onto ice (200 ml) and left until the ice melted. The resulting white solid was filtered off, washed with water, and dissolved in DME (100 ml). The solution was dried over 4A mol. sieves for 1.5 hours, filtered then added to a solution of 3-methylthio-pyridazine[2] (2.6 g) in dichloromethane (35 ml) and the reaction stirred at room temperature for 20 h. The intermediate salt was isolated by filtration as light brown crystals (3.87 g), suspended in acetonitrile (100 ml) and methyl 3-(4fluoro-phenyl)-prop-2-ynoic acid (2.02 g) added. 1,8-Diazabicyclo[5.4.0]undec-7-ene (2.1 ml) was added dropwise and the reaction was stirred at room temperature for 20 hours. The resulting crystalline precipitate was filtered off, washed and dried (770 mg). Concentration of the filtrate gave a second crop (430 mg). The residues were partioned between water and ethyl acetate (100 ml each) and the aqueous layer was extracted with ethyl acetate (20 ml). The combined organics were washed with water, brine and dried. Removal of solvent gave a brown oil which was purified by flash chromatography on silica (300 g) eluting with cyclohexane/ethyl acetate (3:1) to give a further quantity of product (247 mg). The three crops were combined to give the title compound (1.45 g) as a light brown solid.

$MH^+$ 318; 1H NMR ($CDCl_3$) δ 2.70 (3H, s ), 3.88 (3H, s) 7.08–7.18 (3H, m) 7.84 (2H, m) 8.31 (1H, d, J=10 Hz); Ref:[1] K Novitskii et al, Khim Geterotskil Soedin, 1970 2, 57–62; Ref:[2] Barlin G. B., Brown, W. V., J Chem Soc (1968), (12), 1435–45.

(ii) 2-(4-Fluoro-phenyl)-3-(4-methanesulfonyl-phenyl)-6-methylsulfanyl-pyrazolo[1,5-b]pyridazine A mixture of the 2-(4-fluoro-phenyl)-6-(methylthio)-pyrazolo[1,5-b]pyridazine-3-carboxylic acid methyl ester (1.45 g) potassium carbonate (690 mg) in methanol (40 ml) and water (14 ml) was stirred and heated under reflux for 20 hours under nitrogen. The solvents were removed and the resulting solid partioned between ethyl acetate (50 ml) and water (250 ml). The aqueous layer was acidified to pH1 (2MHCl) and a solid was filtered off (1.0 g, MH+ 304). A mixture of the solid (1.0 g), sodium bicarbonate (557 mg) and NBS (594 mg) were stirred at room temperature for 4 hours. The reaction was poured into water (150 ml) and extracted with ethyl acetate (3×50 ml). The combined extracts were washed with water (50 ml), brine (20 ml), dried and concentrated. The resulting solid (1.015 g, MH+ 338,340), 4-(methanesulphonyl)phenyl boronic acid (902 mg), sodium carbonate (740 mg) and tetrakis (triphenylphosphine)palladium(0) (175 mg) were stirred and heated under nitrogen at reflux in DME (30 mls) and water (15 ml) for 48 hours. The reaction was poured into water and extracted with ethyl acetate (3×50 ml). The combined extracts were dried and the solvent removed to give a brown solid. This was purified on silica (300 g) eluting with cyclohexane, ethyl acetate (1:1) to give the title compound (0.713 g) as a yellow solid.

MH+ 414; 1H NMR δ (DMSO) 2.65 (3H, s) 3.28 (3H, s) 7.20 –7.30 (3H, m) 7.55 (2H, m) 7.62 (4H, d, J=8.5 Hz) 7.95–8.05 (3H, m).

(iii) 2-(4-Fluoro-phenyl)-6-methanesulfonyl-3-(4-methanesulfonyl-phenyl)-pyrazolo[1,5-b]pyridazine A suspension of 2-(4-fluoro-phenyl)-3-(4-methanesulfonyl-phenyl)-6-(methylthio)-pyrazolo[1,5-b] pyridazine (60 mg 0.145) in MeOH (5 ml) and water (2 ml) was stirred with oxone (196 mg 0.32) for 20 hours. The resulting solution was poured into water (50 ml) and extracted with chloroform (3×20 ml). The combined extracts were dried and the solvent removed. Crystallisation of the residue from methanol gave the title compound (60 mg) as a white solid.

MH+ 446; 1H NMR (DMSO-$d_6$) δ 3.34 (3H, s) 3.53 (3H, s) 7.33 (2H, t, J=9 Hz) 7.62 (2H, m) 7.68 (1H, d, J=8.5 Hz) 8.04 (1H, d, J=10 Hz) 8.52 (1H, d, J=9 Hz); TLC $SiO_2$ Hexane:Ethyl acetate (1:1) Rf 0.24 UV.

EXAMPLE 5

2-(4-Difluoromethoxy-phenyl)-3-(4-methanesulfonyl-phenyl)-pyrazolo[1,5-b]pyridazine Sodium hydride (48 mg, 60% disp. in oil, 1.2 mmol) was added to a solution of 4-[3-(4-methanesulfonyl-phenyl)-pyrazolo[1,5-b]pyridazin-2-yl]-phenol (200 mg, 0.55 mmol) in anhydrous dimethylformamide (5 ml). Bromodifluoromethane gas was gently bubbled through the solution for 20 min, then diluted with $CH_2Cl_2$ (30 ml). Aqueous workup followed by chromatography on silica gel with $CH_2Cl_2$:ethyl acetate (3:1) as eluant then chromatography with $CH_2Cl_2$:ethyl acetate (10:1) as eluant gave the title compound (63 mg, 28%) as a white solid.

MH+ 416; NMR ($CDCl_3$) δ 8.38 (1H, dd, J=4 Hz), 8.01 (2H, d, J=8.5 Hz), 7.94 (1H, dd, J=9 & 2 Hz), 7.65 (2H, d, J 8.5 Hz) 7.57 (2H, d, J=8 Hz), 7.10 (3H, m), 6.87–6.27 (1H, t, J=7.4 Hz) 3.15 (3H, s).

EXAMPLE 6

4-[2-(4-Ethoxy-phenyl)-pyrazolo[1,5-b]pyridazin-3-yl]-benzenesulfonamide (i) 2-(4-Ethoxy-phenyl)-pyrazolo[1,5-b]pyridazine-3-carboxylic Acid Methyl Ester Diazabicyclo[5.4.0]undec-7-ene (1.47 ml, 2 eq) was added dropwise to a solution of methyl 3-(4-ethoxy-phenyl)-prop-2-ynoic acid (1.0 g) and 1-amino pyridazinium iodide[2] (2.19 g) in acetonitrile (10 ml) under nitrogen and stirred for 5 h. Concentration and aqueous workup gave the title compound (1.2 g) as a sticky brown solid.

MH+ 298.

(ii) 2-(4-Ethoxy-phenyl)-pyrazolo[1,5-b]pyridazine-3-carboxylic Acid

A mixture of 2-(4-ethoxy-phenyl)-pyrazolo[1,5-b] pyridazine-3-carboxylic acid methyl ester (1.2 g), ethanol (10 ml) and 2N sodium hydroxide (10 ml) was heated to 80○ for 1.5 h. The mixture was allowed to cool and acidified to pH 1 with 2N hydrochloric acid. The title compound was isolated by filtration as a brown solid (716 mg, 63%). MH+ 284.

(iii) 2-(4-Ethoxy-phenyl)-3-iodo-pyrazolo[1,5-b]pyridazine

A mixture of 2-(4-ethoxy-phenyl)-pyrazolo[1,5-b] pyridazine-3-carboxylic acid (710 mg), N-iodosuccinimide (678 mg) and sodium bicarbonate (717 mg) in DMF (8 ml) was stirred for 4 h. A further quantity of N-iodosuccinimide (100 mg) was added and stirring continued for 2 h. Aqueous workup gave a dark brown solid which was purified by SPE with dichloromethane as eluant. This gave the title compound as an orange-brown solid (429 mg, 47%).

MH+ 366.

(iv) 4-[2-(4-Ethoxy-phenyl)-pyrazolo[1,5-b]pyridazin-3-yl]-benzenesulfonamide

A mixture of 4-iodobenzenesulphonamide (0.311 g), dipinacoldiborane, (0.279 g), potassium acetate (486 mg) and [1,1'-bis(diphenylphosphino)-ferrocene]palladium(II) chloride complex with dichloromethane (1:1) (0.45 g) in dimethylformamide (8 ml) was heated under nitrogen at 80° for 2 h. The cooled reaction mixture was concentrated in vacuo and the residue suspended in 1,2 dimethoxyethane (10 ml), 2-(4-ethoxy-phenyl)-3-iodo-pyrazolo[1,5-b]pyridazine (0.4 g) was added together with 2N sodium carbonate (4 ml) and tetrakis(triphenylphosphine)palladium(0) (20 mg) and the mixture heated at reflux under nitrogen for 18 hours. The cooled reaction mixture was poured into water (60 ml) and the suspension extracted with ethyl acetate (3×60 ml). The organic extracts were combined, dried ($Na_2SO_4$) and concentrated. The residue was purified by chromatography eluting with dichloromethane/ethyl acetate (3:1) to give the title compound as a yellow solid (0.116 g, 27%).

MH+ 395; NMR ($CDCL_3$) δ 8.32 (1H, dd, J=4 & 2 Hz), 7.97 (2H, d, J=8 Hz), 7.89 (1H, dd, J=9 & 2 Hz), 7.54 (4H, m), 7.04 (1H, dd, J=9 & 4 Hz), 6.88 (2H, d, J=9 Hz), 1.43 (3H, t, J=7 Hz); Ref:[1] R. Miyaura et al J. Org. Chem., 1995, 60, 7508–7510.

EXAMPLE 7

6-Difluoromethoxy-2-(3-fluoro-phenyl)-3-(4-methanesulfonyl-phenyl)-pyrazolo[1,5-b]pyridazine (i) 1-(2,2-Dibromo-vinyl)-3-fluoro-benzene To a stirred cooled (ice/salt, 0°) solution of carbon tetrabromide (48.82 g) in anhydrous $CH_2Cl_2$ (200 ml) was added portionwise over 3 minutes, triphenylphosphine (77.1 g), maintaining the temperature below 10°. The resulting orange suspension was stirred at 0° for 1 hour before adding to it, 3-fluorobenzaldehyde (7.8 ml). After the addition was complete, the suspension was stirred at 0° for 1 hour then quenched by the addition of water (75 ml). The organic phase was separated and washed with brine (75 ml), dried ($Na_2SO_4$) and evaporated to dryness. The residual gum was poured into cyclohexane (1L) and stirred for 30 minutes. The organic phase was decanted and the residue taken up into $CH_2Cl_2$ and poured into cyclohexane (1L). This procedure was repeated twice more and the combined organic phases concentrated to ~100 ml and passed through silica gel. The filtrate was concentrated to give the title compound as a mobile yellow oil (24 g, 100%).

MH⁺ 280, MH⁻ 279; NMR (CDCl₃) δ 7.05 (1H, tm, J=9 Hz) 7.3 (3H, m) 7.45 (1H, s).

(ii) (3-Fluoro-phenyl)-propynoic Acid Methyl Ester

To a stirred solution of 1-(2,2-dibromo-vinyl)-3-fluoro-benzene (23.8 g) in anhydrous THF (350 ml) cooled to −78° was added dropwise over 30 minutes, n-butyllithium (2.2 eq, 1.6M in hexanes). The mixture was stirred for a further 30 minutes at −78° before methyl chloroformate (11.6 g, 9.5 ml) was added and the resultant mixture allowed to warm to 0° for 1 hour before being diluted with 1:1 saturated aqueous sodium bicarbonate:ammonium chloride (100 ml) and extracted into ether (2×100 ml). The combined organic extract was washed with brine (25 ml), dried (Na₂SO₄) and evaporated to dryness to give the title compound as a brown oil (16.7 g, 100%).

MH⁻ 173; NMR (CDCl₃) δ 7.4–7.1 (4H, m) 3.85 (3H, s, CO₂Me).

(iii) 2-(3-Fluoro-phenyl)-6-methoxy-pyrazolo[1,5-b]pyridazine-3-carboxylic Acid Methyl Ester 1,8-Diazabicyclo[5.4.0]undec-7-ene (5 ml) was added to a stirred, chilled, mixture of (3-fluoro-phenyl)-propynoic acid methyl ester (2.67 g) and 1-amino-3-methoxy-pyridazin-1-ium mesitylene sulphonate (4.89 g) in acetonitrile (80 ml) and the mixture was stirred at 0° for 1 hour then at ambient temperature for 18 hours. The mixture was concentrated in vacuo, and partitioned between ethyl acetate (150 ml) and water (150 ml). The aqueous phase was separated and further extracted with ethyl acetate (2×100 ml). The combined organic extracts were washed with water (2×50 ml), brine (25 ml), dried (MgSO₄), filtered and evaporated in vacuo to give a solid which was triturated with anhydrous ether:petroleum ether (1:0.5) to give the title compound as a brown solid (2.4 g, 53%).

MH⁺ 302; 1H NMR (CDCl₃) δ 12.8 (1H, br s); 8.4 (1H, d, J 10 Hz) 7.7–7.6 (2H, m) 7.42 (1H, q, J 8 Hz) 7.15 (1H, td, J 8 & 3 Hz) 6.95 (1H ,d, J 10 Hz) 4.1 (3H, s) 3.88 (3H, s).

(iv) 2-(3-Fluoro-phenyl)6-methoxy-pyrazolo[1,5-b]pyridazine-3-carboxylic Acid 2N sodium hydroxide (50 ml) was added to a solution of 2-(3-fluoro-phenyl)-6-methoxy-pyrazolo[1,5-b]pyridazine-3-carboxylic acid methyl ester (2.3 g) in absolute ethanol (50 ml) and the resulting mixture heated to reflux for three hours. The cooled reaction mixture was poured slowly into a stirred solution of 2N hydrochloric acid (300 ml). The resulting suspension was stirred at ambient temperature for 1 hour then filtered and the filter cake washed with water and dried in vacuo at 600 to give the title compound as an off-white solid (2.0 g, 91%).

MH⁺ 288; 1H NMR (DMSO) δ 8.45 (1H, d, J 10 Hz); 7.67 (2H, m); 7.5 (1H, q, J 7 Hz); 7.3 (1H, td, J 7 & 2 Hz); 7.21 (1H, d, J 10 Hz); 4.0 (3H, s).

(v) 3-Bromo-2-(3-fluoro-phenyl)-6-methoxy-pyrazolo[1,5-b]pyridazine

To a stirred solution of 2-(3-fluoro-phenyl)-6-methoxy-pyrazolo[1,5-b]pyridazine-3-carboxylic acid (2.0 g) in anhydrous DMF (20 ml) was added n-bromosuccinimide (1.78 g) and the resulting solution stirred at ambient temperature for 3 hours. The reaction mixture was diluted with ethyl acetate (800 ml) and washed sequentially with water (10×100 ml) and sat. brine (25 ml), dried (Na₂SO₄), and concentrated to give the title compound as a buff solid (2.19, 93%).

MH⁺ 323, MH⁻ 321; 1H NMR (CDCl₃) 7.9 (2H, m) 7.8 (1H, d, J 10 Hz); 7.45 (1H, m); 7.1 91H, td, J 8 & 2 Hz); 6.78 (1H, d, J 10 Hz); 4.1 (3H, s).

(vi) 6-Difluoromethoxy-2-(3-fluoro-phenyl)-pyrazolo[1,5-b]pyridazine

Portions of 3-bromo-2-(3-fluoro-phenyl)-6-methoxy-pyrazolo[1,5-b]pyridazine (400 mg, 2.1 g total) were placed in individual Reactivials equipped with a magnetic stirrer bar. Pyridine hydrochloride (10 eq) was added to each vial, the vials sealed, and heated to 2000 for 3 hours. The vials were allowed to cool to ~140° before opening and the contents poured into ice/water. The resulting mixture was extracted into ethyl acetate (3×100 ml) and the combined organic extracts washed with water (7×75 ml), dried (Na₂SO₄) and evaporated to give the des-bromo phenol as a brown solid (1.0 g, MH⁺ 230). This solid was dissolved in anhydrous DMF (10 ml) and sodium hydride (60% dispersion in mineral oil, 200 mg) added portionwise. After stirring for 20 minutes at ambient temperature the solution was transferred to a small cooled autoclave and bromodifluoromethane (5 ml, xs, condensed at −30°) added. The autoclave was then sealed, allowed to warm to ambient temperature and stirred for 36 hours. The resulting solution was diluted with ethyl acetate (200 ml), washed with water (10×20 ml), dried (Na₂SO₄), concentrated and the residual gum purified by flash column chromatography with cyclohexane:ethyl acetate (4:1) as eluant. This gave the title compound as a solid (652 mg, 60%).

MH⁺ 280 MH⁻ 278; NMR (DMSO) δ 8.42(1H, d, J=10 Hz) 7.85 (1H, d, J 8 Hz) 7.78 (1H, t, J 70 Hz) 7.55 (1H, q, J 8 Hz) 7.38 (1H, s) 7.25 (1H, m) 7.17 (1H, d, J 10 Hz).

(vii) 3-Bromo-6-difluoromethoxy-2-(3-fluoro-phenyl)-pyrazolo[1,5-b]pyridazine

N-bromo succinimide (195 mg) was added to a solution of 6-difluoromethoxy-2-(3-fluoro-phenyl)-pyrazolo[1,5-b]pyridazine (251 mg) and sodium bicarbonate (185 mg) in anhydrous DMF (10 ml) and stirred for 18 h. The reaction mixture was diluted with ethyl acetate (300 ml) and washed with water (10×20 ml), brine (20 ml), dried (Na₂SO₄) and concentrated to give the title compound as a solid (293 mg, 91%).

MH⁺ 359, MH⁻ 356/357; NMR (DMSO) δ 8.36 (1H, d, J 10 Hz) 7.88 (1H, d, J 8 Hz) 7.78 (1H, t, J 70 Hz, OCHF₂) 7.77 (1H, dm, J 10 Hz) 7.62 (1H, dt, J 8 & 6 Hz) 7.38 (1H, dt, J 9 & 2Hz) 7.3 (1H, d, J 10 Hz).

(viii) 6-Difluoromethoxy-2-(3-fluoro-phenyl)-3-(4-methanesulfonyl-phenyl)-pyrazolo[1,5-b]pyridazine To a stirred solution of 3-bromo-6-difluoromethoxy-2-(3-fluoro-phenyl)-pyrazolo[1,5-b]pyridazine (286 mg) in DMF (20 ml) was added 2N aq sodium carbonate (10 ml). To this mixture was added 4-methanesulfonyl-phenylboronic acid (180 mg) and tetrakis triphenylphosphine palladium(0) (34 mg). The resulting mixture was stirred and heated to reflux for 18 hours. The cooled reaction mixture was diluted with ethyl acetate (300 ml) and the organic solution washed with water (10×30 ml) and brine (30 ml), dried (Na₂SO₄) and evaporated to give a gum which was purified by flash column chromatography with chloroform:ethyl acetate (50:1 to 5:1) as eluant. Combination of appropriate fractions and concentration gave the title compound as an off-white solid (132 mg, 37%).

MH⁺ 434; 1H NMR(CDCl₃) δ 8.02 (1H, d, J 9 Hz); 7.95 (2H, d, J 10 Hz); 7.58 (1H, d, 9 Hz); 7.52 (1H, t, J 70 Hz); 7.32 (3H, m); 7.08 (1H, m); 6.9 (1H, d, J 9 Hz); 3.15 (3H, s).

Biological Data

Inhibitory activity against human COX-1 and COX-2 was assessed in COS cells which had been stably transfected with cDNA for human COX-1 and human COX-2. 24 Hours prior to experiment, COS cells were transferred from the 175 cm² flasks in which they were grown, onto 24-well cell culture plates using the following procedure. The incubation medium (Dulbecco's modified eagles medium (DMEM) supplemented with heat-inactivated foetal calf serum (10% v/v), penicillin (100 IU/ml), streptomycin (100 μg/ml) and geneticin (600 μg/ml)) was removed from a flask of confluent cells (1 flask at confluency contains approximately 1×1 cells). 10 ml of phosphate buffered saline (PBS) was added to the flask to wash the cells. Having discarded the PBS, cells were then rinsed in 10 ml trypsin for 20 seconds, after which the trypsin was removed and the flask placed in an incubator (370) for 1–2 minutes until cells became detached from the flask. The flask was then removed from the incubator and cells resuspended in 10 ml of fresh incubation medium. The contents of the flask was transferred to a 250 ml sterile container and the volume of incubation medium subsequently made up to 100 ml. 1 ml cell suspension was pipetted into each well of 4×24-well cell culture plates. The plates were then placed in an incubator (37° C., 95% air/5% CO₂) overnight. If more than 1 flask of cells were required, the cells from the individual flasks were combined before being dispensed into the 24-well plates.

Following the overnight incubation, the incubation medium was completely removed from the 24-well cell culture plates and replaced with 250 μl fresh DMEM (37° C.). The test compounds were made up to 250× the required test concentration in DMSO and were added to the wells in a volume of 1 μl. Plates were then mixed gently by swirling and then placed in an incubator for 1 hour (37° C., 95% air/5% CO₂). Following the incubation period, 10 μl of arachidonic acid (750 μM) was added to each well to give a final arachidonic acid concentration of 30 μM. Plates were then incubated for a further 15 minutes, after which the incubation medium was removed from each well of the plates and stored at −20° C., prior to determination of prostaglandin $E_2$ (PGE2) levels using enzyme immunoassay. The inhibitory potency of the test compound was expressed as an $IC_{50}$ value, which is defined as the concentration of the compound required to inhibit the PGE2 release from the cells by 50%. The selectivity ratio of inhibition of COX-1 versus COX-2 was calculated by comparing respective $IC_{50}$ values.

The following $IC_{50}$ values for inhibition of COX-2 and COX-1 were obtained for compounds of the invention:

| Example No. | COX-2: $IC_{50}$(nM) | COX-1: $IC_{50}$(nM) |
|---|---|---|
| 1(v) | 35 | >100,000 |
| 2(ii) | <10 | 3,880 |
| 3(ii) | 3 | >100,000 |
| 4(iii) | 370 | >100,000 |
| 5 | 21 | >100,000 |
| 6(iv) | 0.44 | 3828 |
| 7(viii) | 16 | >55,200 |

What is claimed is:
1. Compounds of formula (I)

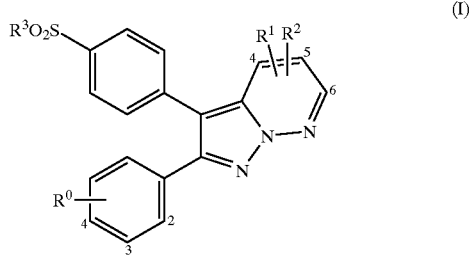

and pharmaceutically acceptable salts, solvates, esters and salts or solvates of such esters, of the compounds of formula (I) which:

$R^0$ is halogen, $C_{1-6}$alkyl, $C_{1-6}$alkoxy, $C_{1-6}$alkoxy substituted by one or more fluorine atoms, or $O(CH_2)_nNR^4R^5$;

$R^1$ and $R^2$ are independently selected from H, $C_{1-6}$alkyl, $C_{1-6}$alkyl substituted by one or more fluorine atoms, $C_{1-6}$alkoxy, $C_{1-6}$hydroxyalkyl, $SC_{1-6}$alkyl, $C(O)H$, $C(O)C_{1-6}$alkyl, $C_{1-6}$alkylsulphonyl, $C_{1-6}$alkoxy substituted by one or more fluorine atoms, $O(CH_2)_nCO_2C_{1-6}$alkyl, $O(CH_2)_nSC_{1-6}$alkyl, $(CH_2)_nNR^4R^5$, $(CH_2)_nSC_{1-6}$alkyl or $C(O)NR^4R^5$; with the proviso that when $R^0$ is at the 4-position and is halogen, at least one of $R^1$ and $R^2$ is $C_{1-6}$alkylsulphonyl, $C_{1-6}$alkoxy substituted by one or more fluorine atoms, $O(CH_2)_nCO_2C_{1-6}$alkyl, $O(CH_2)_nSC_{1-6}$alkyl, $(CH_2)_nNR^4R^5$ or $(CH_2)_nSC_{1-6}$alkyl, $C(O)NR^4R^5$;

$R^3$ is $C_{1-6}$alkyl or $NH_2$;

$R^4$ and $R^5$ are independently selected from H and $C_{1-6}$alkyl; and n is 1–4.

2. Compounds as claimed in claim 1 wherein $R^0$ is F, $C_{1-3}$alkyl, $C_{1-3}$alkoxy, $C_{1-3}$alkoxy substituted by one or more fluorine atoms, or $O(CH_2)_nNR^4R^5$; $R^1$ is $C_{1-4}$alkylsulphonyl, $C_{1-4}$alkoxy substituted by one or more fluorine atoms, $O(CH_2)_nCO_2C_{1-4}$alkyl, $O(CH_2)_nSC_{1-4}$alkyl, $(CH_2)_nNR^4R^5$, $(CH_2)_nSC_{1-4}$alkyl or $C(O)NR^4R^5$ or, when $R^0$ is $C_{1-3}$alkyl, $C_{1-3}$alkoxy, $C_{1-3}$alkoxy substituted by one or more fluorine atoms, or $O(CH_2)_nNR^4R^5$, $R^1$ may also be H; $R^2$ is H; $R^3$ is methyl or $NH_2$; $R^4$ and $R^5$ are independently $C_{1-3}$alkyl.

3. Compounds as claimed in claim 1 wherein $R^0$ is F, methyl, $C_{1-2}$alkoxy, $OCHF_2$, or $O(CH_2)_nNR^4R^5$; $R^1$ is methylsulphonyl, $OCHF_2$, $O(CH_2)_nCO_2C_{1-4}$alkyl, $O(CH_2)_nSCH_3$, $(CH_2)_nNR^4R^5$, $(CH_2)_nSCH_3$ or $C(O)NR^4R^5$ or when $R^0$ is methyl, $C_{1-2}$alkoxy, $OCHF_2$, or $O(CH_2)_nN(CH_3)_2$, $R^1$ may also be H; $R^2$ is H; $R^3$ is methyl or $NH_2$; $R^4$ and $R^5$ are both methyl; and n is 1–2.

4. Compounds as claimed in claim 1 wherein $R^0$ is F, $C_{1-3}$alkoxy or $C_{1-3}$alkoxy substituted by one or more fluorine atoms; $R^1$ is $C_{1-4}$alkylsulphonyl, $C_{1-4}$alkoxy substituted by one or more fluorine atoms or, when $R^1$ is $C_{1-3}$alkoxy or $C_{1-3}$alkoxy substituted by one or more fluorine atoms, $R^1$ may also be H; $R^2$ is H; and $R^3$ is methyl or $NH_2$.

5. Compounds as claimed in claim 1 wherein $R^1$ is at the 3- or 4-position of the phenyl ring.

6. Compounds as claimed in claim 1 wherein $R^1$ is at the 6-position of the pyridazine ring.

7. 2-(4-Ethoxy-phenyl)-3-(4-methanesulfonyl-phenyl)-pyrazolo[1,5-b]pyridazine; 6-Difluoromethoxy-2-(3-fluoro-phenyl)-3-(4-methanesulfonyl-phenyl)-pyrazolo[1,5-b]pyridazine; and pharmaceutically acceptable salts, solvates, esters and salts or solvates of such esters, thereof.

8. A compound selected from the group consisting of:
3-(4-methanesulfonyl-phenyl)-2-(4-methoxy-phenyl)-pyrazolo[1,5-b]pyridazine;
6-difluoromethoxy-2-(4-fluoro-phenyl)-3-(4-methanesulfonyl-phenyl)-pyrazolo[1,5-b]pyridazine;
2-(4-ethoxy-phenyl)-3-(4-methanesulfonyl-phenyl)-pyrazolo[1,5-b]pyridazine;
2-(4-fluoro-phenyl)-6-methanesulfonyl-3-(4-methanesulfonyl-phenyl)-pyrazolo[1,5-b]pyridazine;
2-(4-difluoromethoxy-phenyl)-3-(4-methanesulfonyl-phenyl)-pyrazolo[1,5-b]pyridazine;
4-[2-(4-ethoxy-phenyl)-pyrazolo[1,5-b]pyridazin-3-yl]-benzenesulfonamide; and
6-difluoromethoxy-2-(3-fluoro-phenyl)-3-(4-methanesulfonyl-phenyl)-pyrazolo[1,5-b]pyridazine;
and pharmaceutically acceptable salts, solvates, esters and salts or solvates of such esters, thereof.

9. A process for preparing compounds according to claim 1, comprising reacting a compound of formula (II)

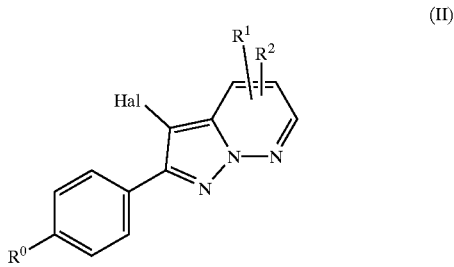

(II)

with a compound of formula (III)

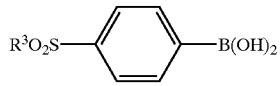

(III)

to prepare a compound of formula (I); and optionally converting the compound of formula (I) into a pharmaceutically acceptable salt, solvate, ester or salt or solvate of such ester, of the compound of formula (I).

10. A process for preparing compounds according to claim 1 where $R^3$ is $C_{1-6}$alkyl, comprising reacting a compound of formula (IV)

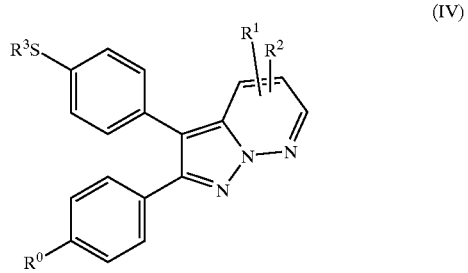

(IV)

with an oxidizing agent to prepare a compound of formula (I); and optionally converting the compound of formula (I) into pharmaceutically acceptable salt, solvate, ester or salt or solvate of such ester, of the compound of formula (I).

11. A process for preparing compounds according to claim 1 where $R^1$ is $C_{1-6}$alkylsulphonyl, comprising oxidizing a compound of formula (V)

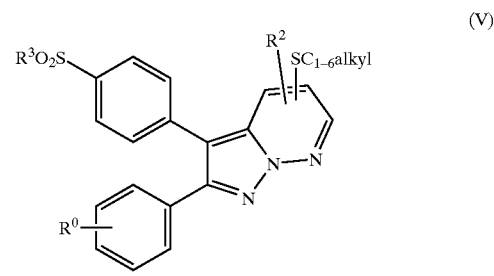

(V)

to prepare a compound of formula (I); and optionally converting the compound of formula (I) into a pharmaceutically acceptable salt, solvate, ester or salt or solvate of such ester, of the compound of formula (I).

12. A process for preparing compounds according to claim 1 where $R^1$ is $C_{1-6}$alkoxy substituted by one or more fluorine atoms, comprising reacting an alcohol of formula (VI)

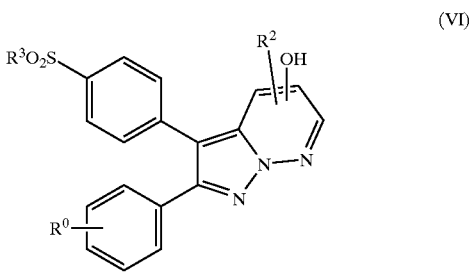

(VI)

with a halofluoroalkane to prepare a compound of formula (I); and optionally converting the compound of formula (I) into a pharmaceutically acceptable salt, solvate, ester or salt or solvate of such ester, of the compound of formula (I).

13. A pharmaceutical composition comprising a compound as defined in claim 1 in admixture with one or more physiologically acceptable carriers or excipients.

14. A pharmaceutical composition comprising a compound as defined in claim 8 in admixture with one or more physiologically acceptable carriers or excipients.

15. A method of treating a subject suffering from a condition which is mediated by selective inhibition of COX-2 which comprises administering to said subject an effective amount of a compound as defined in claim 1.

16. The method according to claim 15, wherein said subject is an animal.

17. The method according to claim 15, wherein said subject is a human.

18. The method according to claim 15, wherein said condition is selected from the group consisting of pain, fever and inflammation.

19. The method according to claim 15, wherein said condition is selected from the group consisting of rheumatic fever, influenza, cold, lower back pain, neck pain, headache, toothache, sprains, strains, myositis, neuralgia, synovitis, arthritis, rheumatoid arthritis, degenerative joint diseases, osteoarthritis, gout, ankylosing spondylitis, tendinitis, bursitis, psoriasis, eczema, burns, dermatitis, sports injuries, and injuries arising from surgical and dental procedures.

20. The method according to claim 15 wherein the condition is an inflammatory disorder.

21. The method according to claim 15 wherein the condition is arthritis.

22. The method according to claim 15 wherein the condition is rheumatoid arthritis or osteoarthritis.

23. The method according to claim 15 wherein the condition is migraine.

24. The method according to claim 15 wherein the condition is multiple sclerosis.

25. A method of treating a subject suffering from a condition which is mediated by selective inhibition of COX-2 which comprises administering to said subject an effective amount of a compound according to claim 9.

26. The method according to claim 25, wherein said subject is an animal.

27. The method according to claim 25, wherein said subject is a human.

28. The method according to claim 25, wherein said condition is selected from the group consisting of pain, fever and inflammation.

29. The method according to claim 25, wherein said condition is selected from the group consisting of rheumatic fever, influenza, cold, lower back pain, neck pain, headache, toothache, sprains, strains, myositis, neuralgia, synovitis, arthritis, rheumatoid arthritis, degenerative joint diseases, osteoarthritis, gout, ankylosing spondylitis, tendinitis, bursitis, psoriasis, eczema, burns, dermatitis, sports injuries, and injuries arising from surgical and dental procedures.

30. The method according to claim 25 wherein the condition is an inflammatory disorder.

31. The method according to claim 25 wherein the condition is arthritis.

32. The method according to claim 25 wherein the condition is rheumatoid arthritis or osteoarthritis.

33. The method according to claim 25 wherein the condition is inflammation in migraine.

34. The method according to claim 25 wherein the condition is inflammation in multiple sclerosis.

* * * * *

UNITED STATES PATENT AND TRADEMARK OFFICE
CERTIFICATE OF CORRECTION

PATENT NO. : 6,451,794 B1
DATED : September 17, 2002
INVENTOR(S) : Beswick et al.

It is certified that error appears in the above-identified patent and that said Letters Patent is hereby corrected as shown below:

Column 18,
Line 26, reads: "$C_{1-6}$alkyl, $O(CH_2)_nSC_{1-6}$alkyl, $(CH_2)_nNR^4R^5$," should read
-- $C_{1-6}$alkyl, $O(CH_2)_nSC_{1-6}$alkyl, $(CH_2)_n NR^4R^5$, --
Line 56, reads: "by one or more fluorine atoms or, when $R^1$ is $C_{1-3}$alkoxy or" should read -- by one or more fluorine atoms or, when $R^0$ is $C_{1-3}$alkoxy or --
Line 59, reads: "Compounds as claimed in claim 1 wherein $R^1$ is at the" should read -- Compounds as claimed in claim 1 wherein $R^0$ is at the --

Column 21,
Line 2, reads: "dition is migraine" should read -- dition is inflammation in migraine --
Line 4, reads: "dition is multiple sclerosis" should read -- dition is inflammation in multiple sclerosis --
Line 8, reads: "effective amount of a compound according to claim 9" should read -- effective amount of a compound according to claim 8 --

Signed and Sealed this

Fifth Day of August, 2003

JAMES E. ROGAN
*Director of the United States Patent and Trademark Office*